Figure 1:
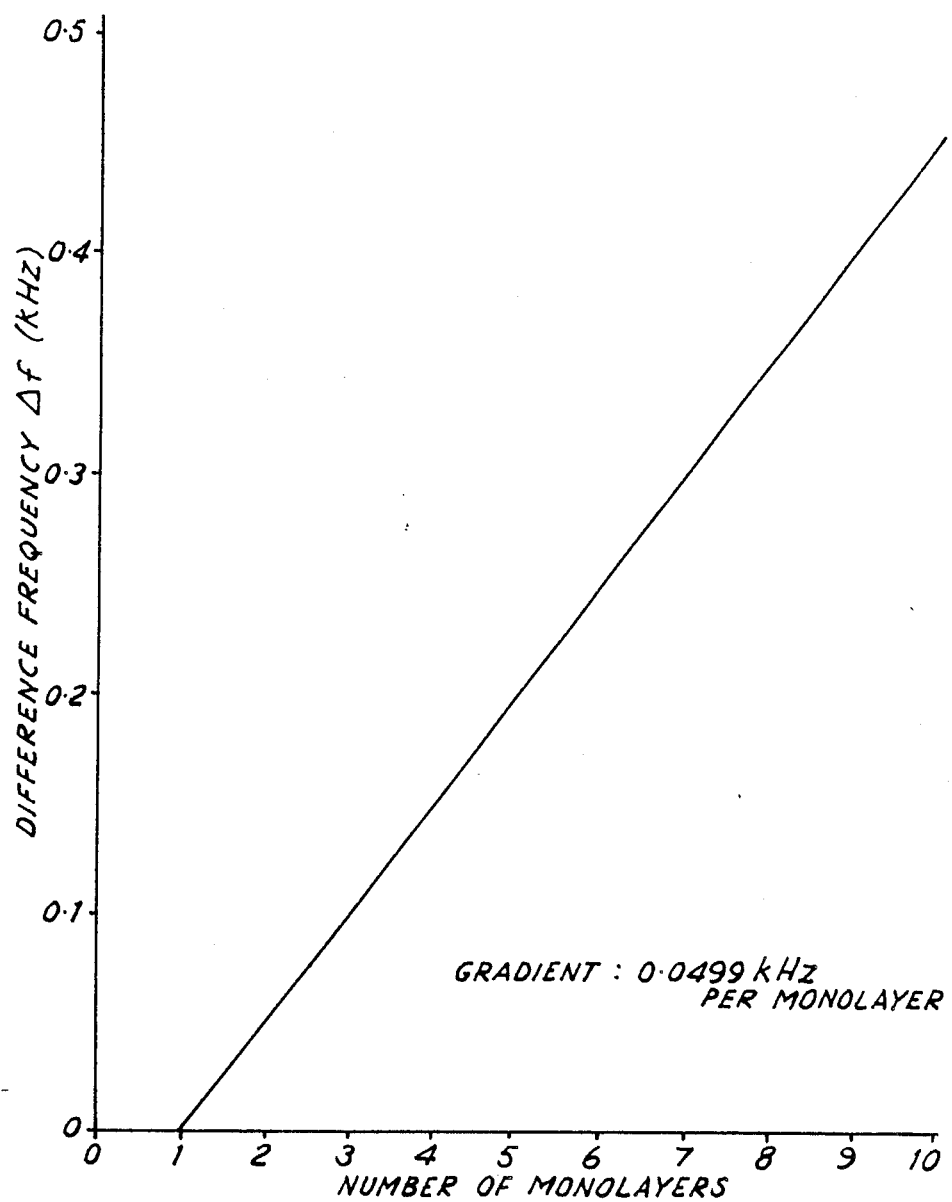

United States Patent [19]

Davies et al.

[11] Patent Number: 4,981,984

[45] Date of Patent: Jan. 1, 1991

[54] ORGANIC COMPOUNDS

[75] Inventors: Stephen G. Davies; Timothy Richardson, both of Oxford; Gareth G. Roberts, Buckinghamshire; Mario E. C. Polywka, Oxford, all of England

[73] Assignee: Thorn Emi plc, London, United Kingdom

[21] Appl. No.: 223,050

[22] Filed: Jul. 22, 1988

[30] Foreign Application Priority Data

Jul. 24, 1987 [GB] United Kingdom ............ 8717566

[51] Int. Cl.$^5$ .................. C07F 9/15; C07F 15/00
[52] U.S. Cl. .................. 556/22; 556/7; 556/13; 556/14; 556/16; 556/30; 427/434.3; 428/411.1; 428/688; 428/690; 428/704
[58] Field of Search .......... 556/22, 7, 13, 14, 16, 556/30; 427/434.3; 428/411.1, 688, 690, 704

[56] References Cited

FOREIGN PATENT DOCUMENTS 0301725  2/1989  European Pat. Off. ............ 556/22

OTHER PUBLICATIONS

"On the History of Langmuir-Blodgett Films", by G. Gaines, Jr. Thin Solid Films 99 (1983), pp. 4–8.
1986 Proc. Int. Symp. on the Applications of Ferroelectric Materials, Philadelphia, by D. Neal et al.
J. Chem. Soc. (1), 1971, 2376, by T. Blackmore et al.

Primary Examiner—Paul F. Shaver
Attorney, Agent, or Firm—Fleit, Jacobson, Cohn, Price, Holman & Stern

[57] ABSTRACT

Langmuir Blodgett films are provided having second order molecular hyperpolarizability of at least $30.10^{-50} C^3 m^3 J^{-2}$. combined with chemical stability and a melting point of over 70°.

They also have desirable pyroelectric properties shown by a static pyroelectric coefficient of at least 0.0039 $nCcm^2k^{-1}$. The films comprise compounds of the following formula:

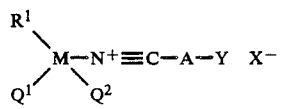

wherein M is ruthenium, iron or cobalt;
R$^1$ is cyclopentadienyl, methylcyclopentadienyl, pentamethylcyclopentadienyl or indenyl;
A$^1$ is (R$^2$)$_3$Z or carbonyl;
Q$^2$ is (R$^2$)$_3$Z or carbonyl;
Z is phosphorus or arsenic;
R$^2$ is an aryl of alkyl radical;
A is

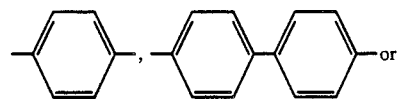

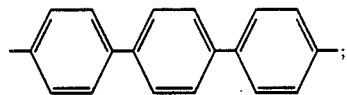

Y is a straight chain alkyl or alkoxy radical comprising from 3 to 17 carbon atoms, or, when A is

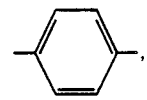

N(R$^3$)$_2$;
R$^3$ is a lower alkyl radical comprising up to 5 carbon atoms; and
X is PF$_6$ or BF$_4$.

18 Claims, 6 Drawing Sheets

ORGANIC COMPOUNDS

This invention relates to organo metallic compounds and to Langmuir-Blodgett films comprising the said compounds, which films possess improved properties. It further relates to useful devices comprising said films.

The formation of Langmuir-Blodgett films of relatively long chain bi-polar molecules is well known. It is further known that certain of these molecules, for example those involving such compounds as hemicyanine or nitrostilbene possess second order molecular hyperpolarizability (literature reference : 1986 Proc. Int. Symp on the Applications of Ferroelectric Materials, Philadelphia by D. Neal et al).

It is an object of the present invention to provide Langmuir-Blodgett films which possess a combination of properties superior to those of the prior art. These films are based on organo metallic compounds of enhanced second order molecular hyperpolarisability combined with improved stability.

Accordingly we provide organo metallic compounds of the following formula:

$$\begin{array}{c} R^1 \\ | \\ M-N^+\equiv C-A-Y \quad X^- \\ / \ \backslash \\ Q^1 \quad Q^2 \end{array}$$

wherein M is ruthenium, iron or cobalt;
R$^1$ is cyclopentadienyl, methylcyclopentadienyl, pentamethylcyclopentadienyl or indenyl;
Q$^1$ is (R$^2$)$_3$Z or carbonyl;
Q$^2$ is (R$^2$)$_3$Z or carbonyl;
Z is phorphorus or arsenic;
R$^2$ is an aryl or an alkyl radical;
A is

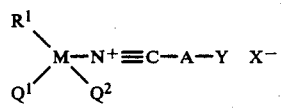

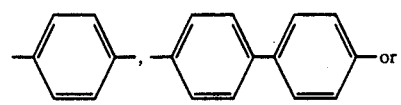

Y is a straight chain alkyl or alkoxy radical comprising from three to seventeen carbon atoms, or, when A is

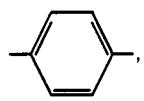

N(R$^3$)$_2$;
R$^3$ is a lower alkyl radical comprising up to five carbon atoms
X$^-$ is PF$_6^-$ or BF$_4^-$.
Most suitably M is ruthenium;
R$_1^1$ is cyclopentadienyl;
Q and Q are both triphenyl phosphinyl;
A-Y is

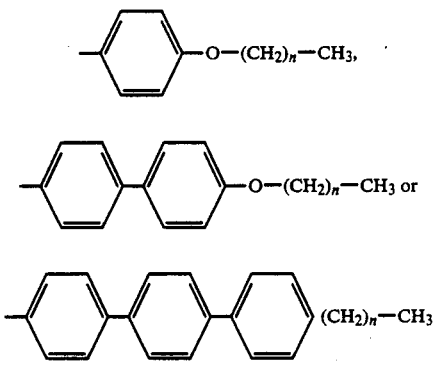

where n is from 2 to 16; and
X$^-$ is PF$_6^-$

Compounds which are found to be particularly useful include:

COMPOUND I

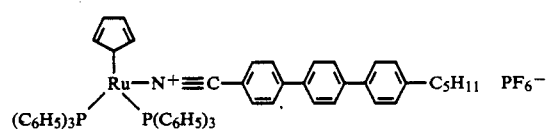

COMPOUND II

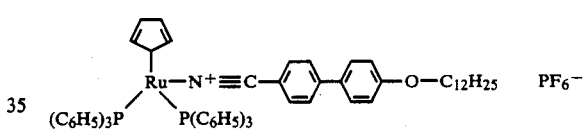

COMPOUND III

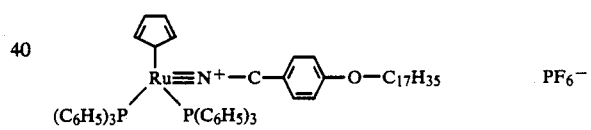

COMPOUND IV

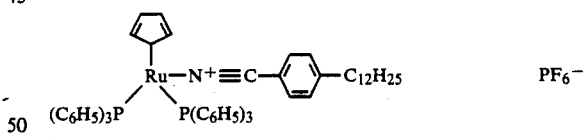

COMPOUND V

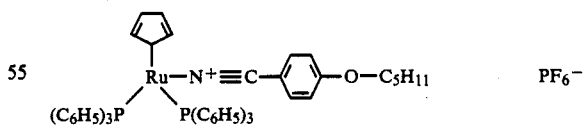

COMPOUND VI

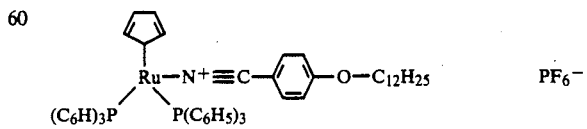

The preparation of films comprising the Compounds I to VI are described in the specific examples hereinbelow:

EXAMPLE 1

5 millimoles of the compound of the formula

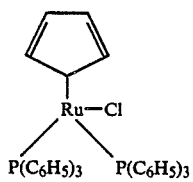

(prepared according to the description in Australian Journal of Chemistry 1977 Volume 30, p.1601 by M. I. Bruce, N. J. Windsor) and 4.5. millimoles of the compound of the formula

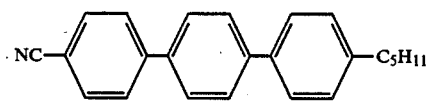

in 20ml of methanol containing 15 millimoles of ammonium hexafluorophine ($NH_4PF_6$) was refluxed under nitrogen for two hours (according to the procedure in J.Chem.Soc. (A), 1971, 2376, T. Blackmore, M. I. Bruce and F. G. A. Stone). After stirring at 20° for 8 hours the solvent was removed by vacuum evaporation and the residue chromatographed on Grade V alumina, using as solvent actone/$NH_4PF_6$ Yellow crystals of compound I in 90% yield (based on the nitrile) were obtained. This product was characterised by a melting point of 108°–110° C. and an n.m.r. analysis of:

$^1$H n.m.r. (300MHz: $CD_3COCD_3$); delta 7.95–7.30 (42H, m, Ph), 4.78 (5H, s, $C_5H_5$), 2.68 (2H, t, J 7.78z, $C_6H_4CH_2$), 1.82–1.35 (6H, m, $-C_2CH_2CH_2-$), 0.91 (3H, t, J 6.7Hz, $CH_2-CH_3$).

EXAMPLE 2

The procedure of Example I was repeated except that instead of 4.5 millimoles of

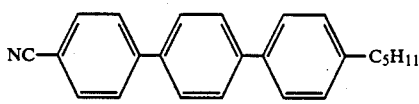

there was used 4.5 millimoles of

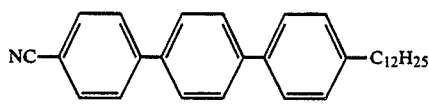

The product was characterised by a melting point of 86° C. and an n.m.r. analysis of:

$^1$H n.m.r. (300MHz: $CD_3COCD_3$); delta 7.9–7.1 (388, m, Ph), 4.78(5H, s, $C_5H_5$), 4.09(2H, t, J 6.5Hz, $OCH_2$), 1.85–1.21 (20H, m, $(CH_2)_{10}$), 0.89(3H, t, J 6.8Hz, $CH_3$).

EXAMPLE 3

The procedure of Example I was repeated except that instead of 4.5 millimoles of

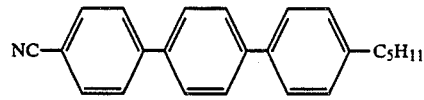

there was used 4.5 millimoles of

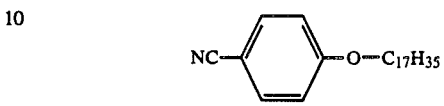

The product was characterised by a melting point of 78° C. and an n.m.r. analysis of:

$^1$H n.m.r. (300MHz: $CD_3COCD_3$); delta 7.50–7.05 (34H, m, Ph), 4.79(5H, s, $C_5H_5$), 4.13(2H, t, J 6.5Hz, $OCH_2$), 1.49–1.21 (30H, m, $(CH_2)_{15}$), 0.89(3H, t, J 6.9Hz, $CH_3$).

EXAMPLE 4

The procedure of Example I was repeated except that instead of 4.5 millimoles of

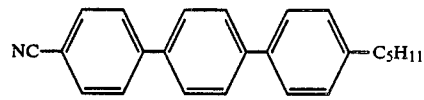

there was used 4.5. millimoles of

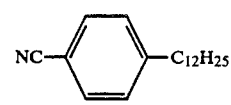

EXAMPLE 5

The procedure of Example I was repeated except that instead of 4.5 millimoles of

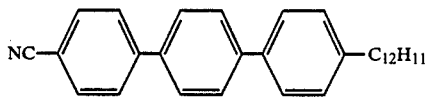

there was used 4.5 millimoles of

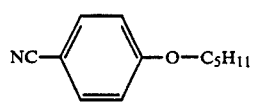

The product was characterised by a melting point of 121° C.

EXAMPLE 6

The procedure of Example I was repeated except that instead of 4.5 millimoles of

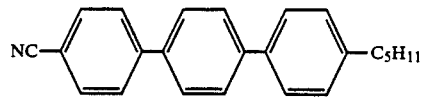

there was used 4.5 millimoles of

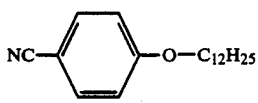

The product was characterised by a melting point of 86° C.

Using the compound prepared in Example 1, a Langmuir-Blodgett film was prepared in the following manner. Approximately 0.5 mg of compound I is dissolved in 10 ml of Aristar grade chloroform. Between 100 and 200µl of this is applied dropwise to a clean (Milli-Q water system) water surface. A PTFE-coated fabric barrier confines the spreading layer to a known surface area. Evaporation of the solvent leaves behind a floating single layer of molecules which may be compressed by reducing the trough area available for the film.

Withdrawal and insertion, typically at 2mm per minute, of a substrate through the compressed film leads to transfer from the liquid-air interface to the substrate. The surface-pressure of the floating film is held at a constant value by means of a feedback mechanism which reduces the trough area available to the film in accordance with the amount of film deposited. In this way Z-type deposition at a surface-pressure of 46m $Nm^{-1}$ is achieved.

Repetition of this procedure a further four times produced a five layer Langmuir-Blodgett film (hereinafter referred to as Film 1) incorporating the compound of Example 1.

In order to produce a Langmuir-Blodgett film incorporating the compounds prepared in Examples 2 to 6, the film-production procedure mentioned above in relation to the compound produced in Example 1 is repeated, with the compounds produced in Examples 2 to 6 being substituted for the compound produced in Example 1. The resultant five layer Langmuir-Blodgett films and hereinafter referred to as Films 2 to 6.

In a slightly refined procedure, the water, to the surface of which the compounds are applied, contains from $5.10^4$ to $1.5.10^{-3}$ moles/litre of cadmium chloride.

This refinement leads to an increase in the area stability of the compounds; for example, the compound prepared in Example 5 exhibits, under these conditions an area per molecule of 150 square angstroms which is within 10 per cent of the theorectical value obtained from a CPK space-filled molecular model.

Also when cadmium chloride is used, a withdrawal and insertion rate of 7 mm per minute may be used.

Samples of above Films were submitted to a number of tests, the results of which are as follows. Firstly, a sample of Film 1 was measured for optical absorbance at 20° C., giving a value of 0.041 absorbance units at 332 nm for five layers; thereafter the film was heated for 90 minutes at 95° C., and then measured again, giving a value of 0.040 absorbance units at 332 nm for five layers. This test indicates that a sample of Film 1 has good thermal stability. It will of course be observed that the relatively high melting point of compound I, compared with certain prior art materials, is an essential pre-requisite for this property.

By making appropriate measurements intermediate to the formation of each of the five layers, a measure of the uniformity per layer is obtained. For example the optical absorbance at 332 nm and 20° C. shows a linear build-up to the value of 0.041 quoted above. In another set of measurements, after the application of each layer to a quartz crystal osillator acting as the substrate, the resonant frequency of the combined structure is measured. According to Sauerbrey's Law, the change in resonant frequency ( f) is proportional to the increase in the mass of the structure; thus, a graph of the difference in resonant frequency f against the number of layers as a multi-layer film is formed, provides an indication of the degree of uniformity of the layers being produced. FIG. 1 shows the results obtained in relation to a film for Sample 1, as measured by reference to the first layer, the straight line of the graph indicating that the layers are substantially equal in mass.

Figure 2:
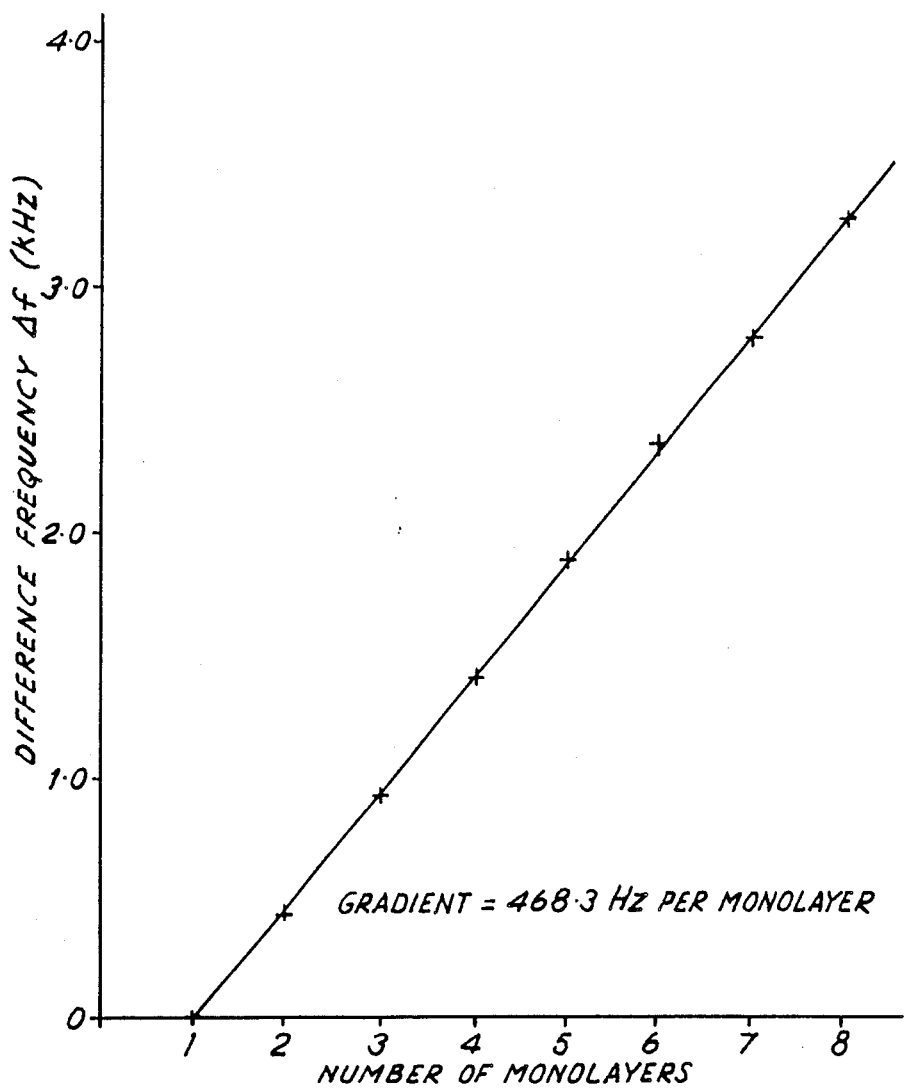

The same set of measurements were made in relation to a multi-layer sample of Film 2, the resultant values being shown by the graph of FIG. 2. Again, these results indicate that the layers are substantially equal in mass.

Figure 3:
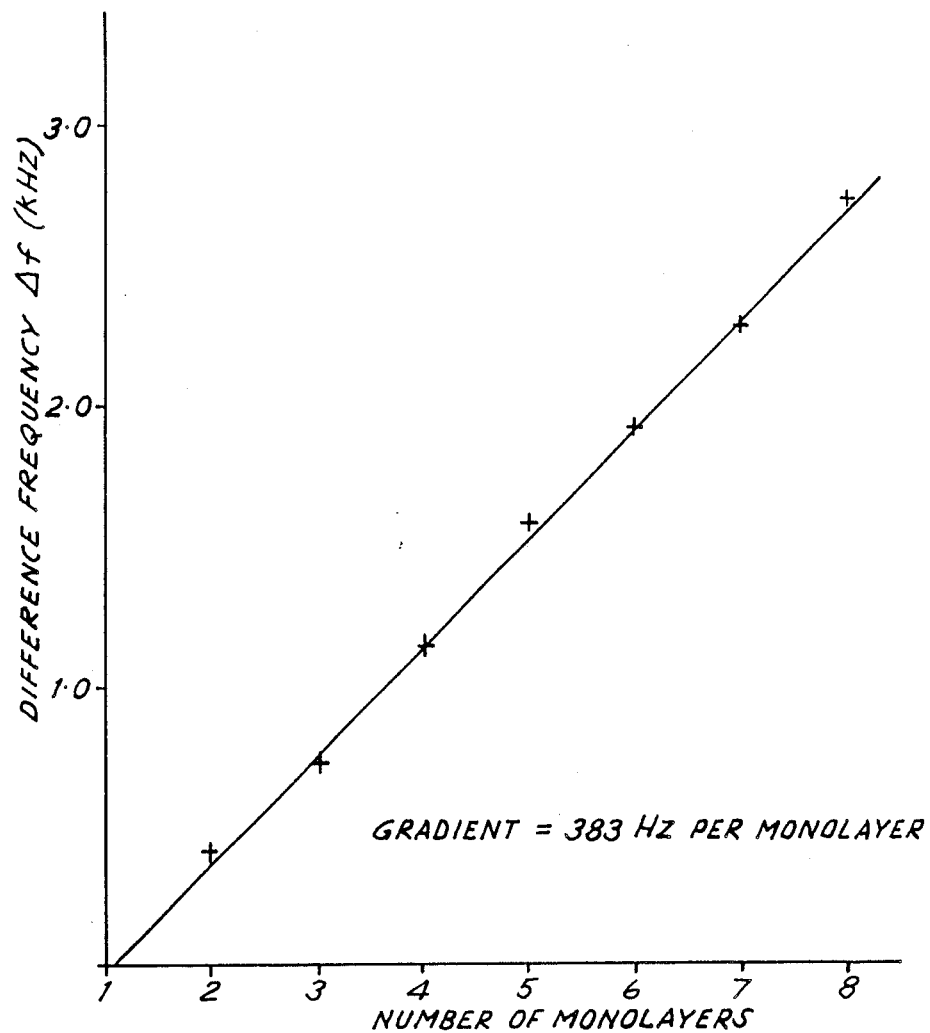

The same set of measurements were made in relation to a multi-layer sample of Film 3, the resultant values being shown by the graph of FIG. 3. Again, these results indicate that the layers are substantially equal in mass. Similar results were obtained for films 4 to 6.

Figure 4:
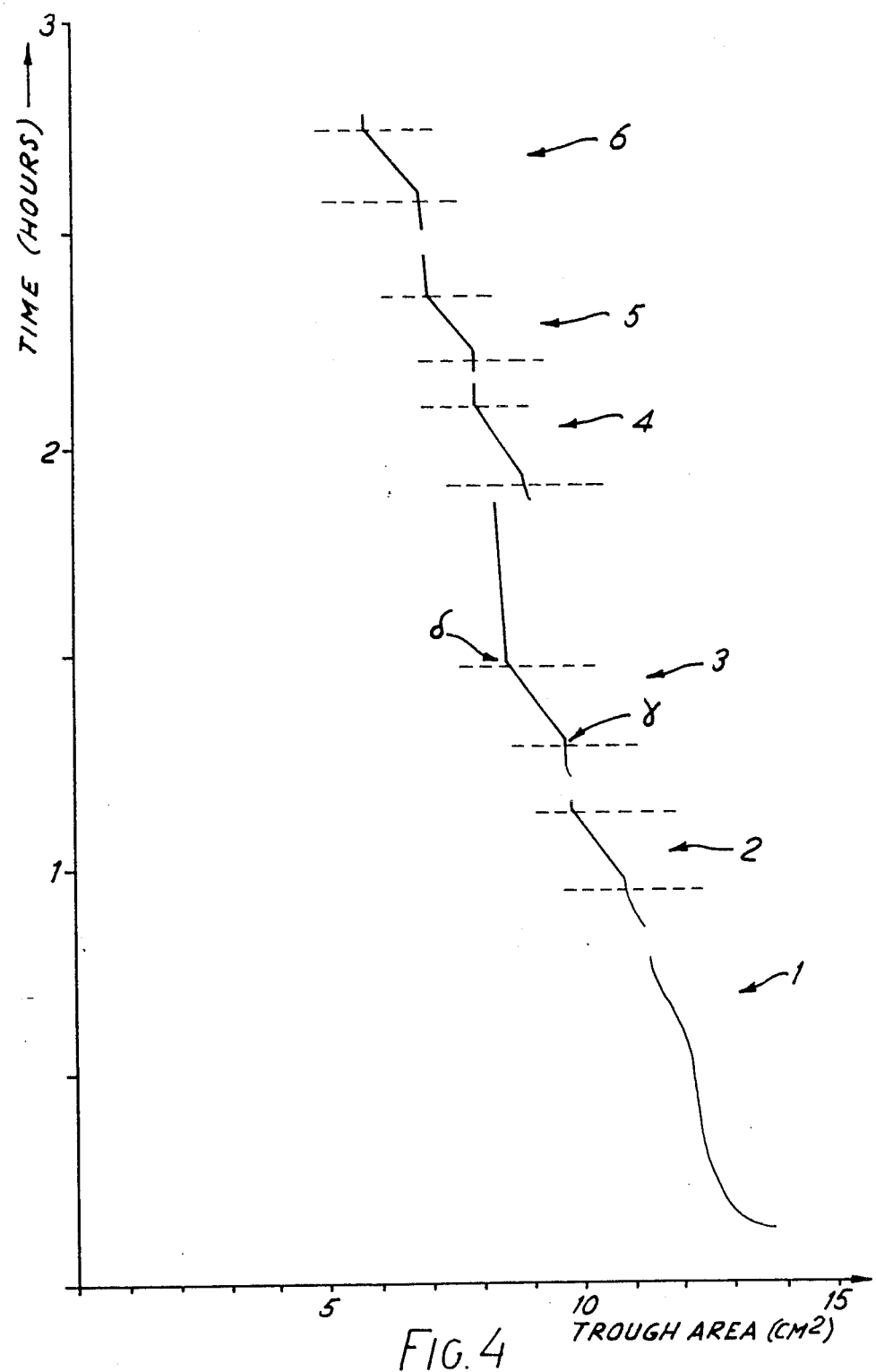
Figure 5:
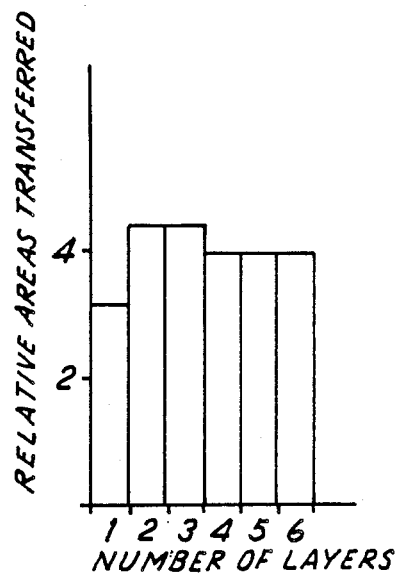

Another test involved the measurement, for the deposition of each of a number of layers, of the trough area against time for a given substrate insertion/withdrawal speed. FIG. 4 shows the resultant graph for the deposition of six layers of a sample of Film 1, and FIG. 5 the integrated values between points gamma and delta for each curve, being an indication of the amount of material deposited.

The first layer was deposited at a speed of 1.3 mm per minute, while the subsequent layers were deposited at a speed of 2.0 mm per minute, so a direct comparison between the results of the first layer and the subsequent layers is not appropriate. In FIG. 4, as shown in relation to layer 3, gamma is the point, in the curve of the deposition of a layer, at which the deposition onto the substrate starts, while delta is the point at which the deposition stops. Between these two points the gradient of the line is substantially constant (i.e. the line is substantially straight); also this gradient has substantially the same value as the corresponding gradients for other layers. These results indicate that uniform layers can be readily and reliably produced.

Figure 6:
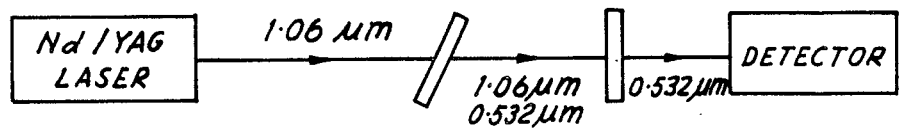
Figure 7:
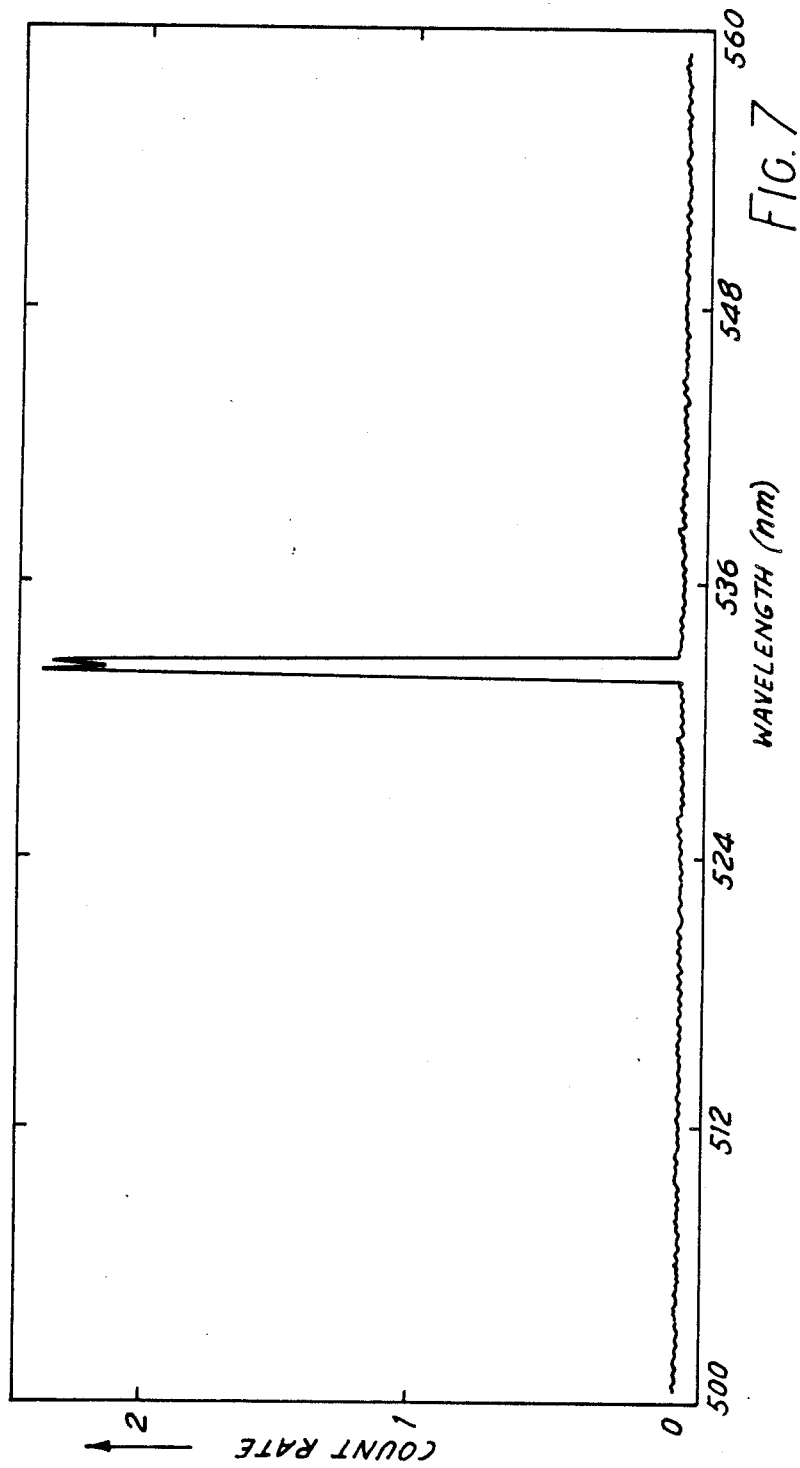

In another test, the second-order molecular hyperpolarisability, beta, of samples of Films 1, 2 and 3 were measured using the equipment shown in FIG. 6. The spectral response is shown 7 and clearly indicates the two to one relationship between the incident laser light of 1064 nm and the radiation wavelength of 532 nm. After appropriate calibration in relation to known values of nitrostilbene and hemicyanine, the results being shown in Table 1 which includes corresponding values of conventional compounds for comparison purposes.

TABLE 1

| Material | Beta ($\times 10^{-50}$ $C^3m^3J^{-2}$) |
|---|---|
| Nitrostilbene | 22 |
| Hemicyanine | 116 |
| Film 1 | 35 |
| Film 2 | 418 |
| Film 3 | 3040 |

Compounds of the present invention may also be used to produce Langmuir-Blodgett films applicable for use in pyroelectric devices. Preferably, an appropriate Langmuir-Blodgett film comprises alternate layers of a compound of the present invention and of a fatty acid, advantageously stearic acid, arachidic acid, behenic acid or tricosanoic acid.

Langmuir-Blodgett films (hereinafter referred to as Films 7 to 12) particularly suited for use in pyroelectric applications are formed of alternate layers of the compound produced in Examples 1 to 6 and omega-tricosenoic acid. Each layer is prepared by the above-mentioned film-production procedure using solutions of the respective compounds produced in Examples 1 to 6 and omega-tricosenoic acid as appropriate, in an alternate-layer Langmuir trough with Z-type deposition for the compound produced in Examples 1 to 6 and with X-type deposition for the omega-tricosenoic.

In another example of a film (hereinafter referred to as Film 13) particularly suited for use in pyroelectric applications, alternate layers of the compound produced in Example 3 and behenic acid are deposited by the above method. In a further modification the compound produced in Example 3 is mixed with varying percentages of behenic acid which mixture is then used in forming alternate layers with behenic acid and giving films 13A, 13B, 13C, 13D and 13E in which the molar proportions of behenic acid mixed with one mole of the compound produced in Example 3 are respectively 1, 0.9, 0.7, 0.3 and 0.1.

The static pyroelectric coefficient of a sample of Films 7 to 12 were measured (using an appropriate standard procedure) and gave the results shown in the following table:

| Film No. | Pyroelectric Coefficient $nCcm^{-2}K^{-1}$ |
|---|---|
| 7 | 0.0085 |
| 8 | 0.0039 |
| 9 | 0.0455 |
| 10 | 0.0245 |
| 11 | 0.0380 |
| 12 | 0.0400 |

Films 13 were also measured and gave the following static pyroelectric coefficients:

| Film No. | Pyroelectric Coefficient $nCcm^{-2}K^{-1}$ |
|---|---|
| 13A | 0.046 |
| 13B | 0.021 |
| 13C | 0.274 |
| 13D | 0.093 |
| 13E | 0.018 |

From this table it will be seen that the optimum proportion of behenic acid to the compound produced in Example 3 is 0.7 to 0.9 moles.

The films 7 to 13, and film 13 in particular, possess additionally the general ruggedness properties (e.g. chemical stability, thermal stabilitY and adhesive/cohesive invariance) which makes them particularly suited to pyroelectric applications as compared to conventional pyroelectric films. Moreover, Films 13 have a low dielectric constant characteristic, rendering them very useful in pyroelectric applications. For comparison, PVDF is considered to have a high value of static pyroelectric coefficient, being of the order of 3.0 nanoCoulombs $Cm^{-2}$ for the material when in a polymer film form; however, because its relative dielectric constant (typically of a value in the order of hundreds) is high in relation to that of Films 13 (typically less than 6), PVDF is impractical in pyroelectric applications.

In another test, a body having a sticky coating, formed by a strip of Sellotape (Registered Trademark), was pressed against a sample of Film 1 on a substrate such that there was secure adhesion. Thereafter the strip was torn away from the substrate, the latter then being examined to determine any change in the condition of Film 1 (for example by using the principles of the Beer-Lambert's Law in order to detect any change in optical absorbance frequency due to change in the film thickness); no changes (to an accuracy of 5%) were detected; accordingly, under this test the Film 1 is considered to have adhesive and cohesive invariance to this accuracy. The test was repeated for Films 2 to 13 and again no changes in the respective Films were detected; thus, again, these films displayed adhesive and cohesive invariance. Films of nitrostilbene or hemicyanine are destroyed when subjected to such a test and therefore do not have adhesive or cohesive invariance. Thus the results of this test indicate that the Films 1 to 13 have good adhesion to the substrate, and that the layers within a multi-layer sample of Films 1 to 13 have good cohesion.

In another test, the optical absorbance and the beta values of samples of Films 1 to 13 were monitored for time degradation, by regular measurement once every fourteen days for six months. No change in values (to an accuracy of 10%) were recorded. Films of nitrostilbene or hemicyanine exhibit significant degradation in condition and performance when subjected to such a test. Thus the compounds have a much improved chemical stability and shelf-life as compared to conventional compounds.

As can be seen from the above, the compounds provided by this invention and the Langmuir-Blodgett films formed therefrom have an outstanding combination of properties, not previously available.

Accordingly our invention also comprises Langmuir-Blodgett films comprising organo metallic compounds possessing, in combination:
  a value of second-order molecular hyperpolasizability of at least $30 \times 10^{-50} C^3 m^3 J^{-2}$;
  a melting point above 70°;
  a chemical stability, to an accuracy of 10%, over a period of substantially six months;
  adhesive and/or cohesive invariance.

Our preferred films comprise compounds having a value of second-order molecular hyperpolarisability of from 300 to 3500 $\times 10^{-50} C^3 m^3 J^{-2}$.

Our invention also comprises Langmuir-Blodgett films comprising ruthenium organo metallic compounds possessing:
  a static pyroelectric coefficient of at least 0.0039 $nCcm^{-2}K^{-1}$ and,
  at least one of the following properties:
  a low dielectric constant;
  a chemical stability, to an accuracy of 10% over a period of substantially six months; adhesive invariance; cohesive invariance.

Our preferred films comprise compounds having a static pyroelectric coefficient of from 0.02 to 0.30, advantageously 0.035 to 0.30 $nCcm^{-2}K^{-1}$.

The films of our invention are very useful. They can be deposited on many forms of substrate, for example glass, alumina, silicon. Moreover, the second-order optical non-linear characteristics of the films of our invention (typified by the values of beta achieved) render it suitable to all those situations and technologies recognised as appropriate applications of devices which exhibit second-order non-linear characteristics. Thus the films of the present invention are particularly suited in electronic devices to achieve parametric amplification without the need for any electron-photon conversion process. Additionally, there are numerous applications in semiconductor technology (for example to change the effective barrier height at a semiconductor surface), in pyroelectric devices, in sensor and in piezoelectric e.g. acoustoelectric devices.

We claim:

1. Organo metallic compounds for use in the production of Langmuir-Blodgett films of the following formula:

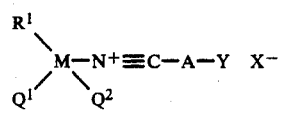

wherein M is ruthenium;
$R^1$ is cyclopentadienyl, methylcyclopentadienyl, pentamethylcyclopentadienyl or indenyl;
$Q^1$ is $(R^2)_cZ$;
$Q^2$ is $(R^2)_3Z$;
Z is phosphorus;
$R^2$ is an aryl or alkyl radical;
A is

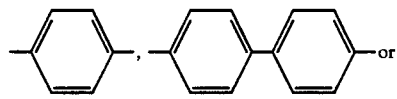

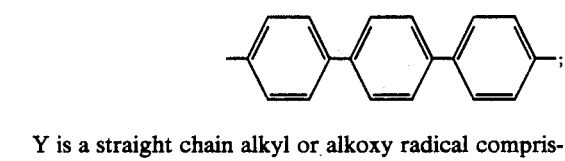

Y is a straight chain alkyl or alkoxy radical comprising from 3 to 17 carbon atoms, or when A is

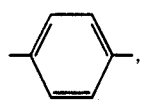

$N(R^3)_2$;
$R_3$ is a lower alkyl radical comprising up to 5 carbon atoms; and
X is $PF_6$ or $BF_4$.

2. Compounds according to claim 1 wherein:
M is ruthenium;
$R^1$ is cyclopentadienyl;
$Q^1$ and $Q^2$ are both triphenylphosphinyl;
A–Y is

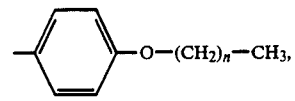

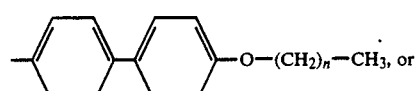

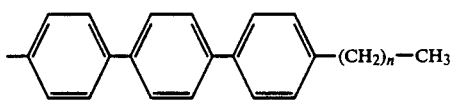

where n is from 2 to 16; and
X is $PF_6$.

3. Compounds according to claim 2 wherein A–Y is

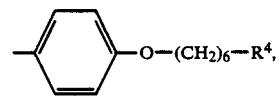

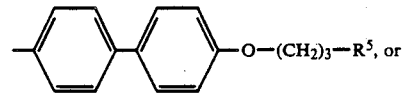

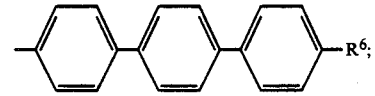

where $R^4$ is a straight chain alkyl radical containing from 5 to 11 carbon atoms;
$R^5$ is a straight chain alkyl radical containing from 5 to 14 carbon atoms; and
$R^6$ is a straight chain alkyl radical containing from 5 to 15 carbon atoms.

4. A compound according to claim 1 of the formula:

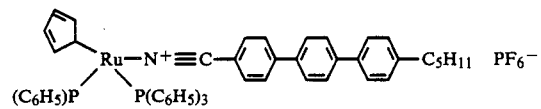

5. A compound according to claim 1 of the formula:

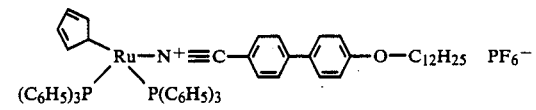

6. A compound according to claim 1 of the formula:

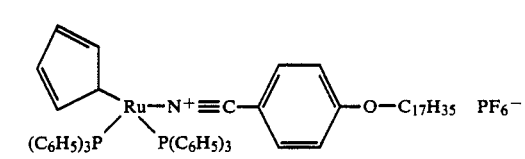

7. A compound according to claim 1 of the formula:

8. A compound according to claim 1 of the formula:

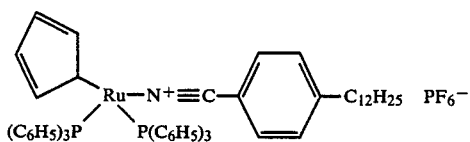

9. A compound according to claim 1 of the formula:

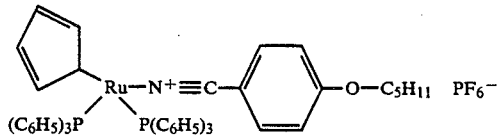

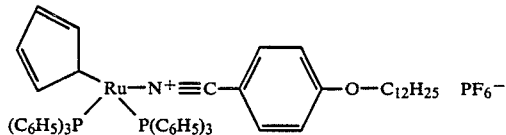

10. A Langmuir-Blodgett film made up of at least one layer comprising a compound according to claim 1.

11. A film according to claim 10 comprising a plurality of said layers and wherein each layer is alternated with a layer of a fatty acid such as stearic, arachidic, behenic or tricosanoic acid.

12. A film according to claim 10 wherein the said layer or layers comprising the compound according to claim 1 also contains a fatty acid such as stearic, arachidic, behenic or tricosanoic acid.

13. A film according to claim 12 wherein said fatty acid is behenic acid and the molar ratio of the behenic acid to the said compound is from 0.7 to 1.0 to 0.9 to 1.0.

14. A chemically stable, cohesively and adhesively invariant Langmuir-Blodgett film according to claim 10 possessing:
a value of second order hyperpolarisability of at least $30.10^{-50}C^3m^3J^{-2}$; and
a melting point above 70° C.

15. A Langmuir-Blodgett film according to claim 14 wherein the value of second order hyperpolarisability is from 300 to 3500 $10^{-50}C^3m^3J^{-2}$.

16. A chemically stable, cohesively and adhesively invariant Langmuir-Blodgett film according to claim 10 possessing a static pyroelectric coefficient of at least $0.0039\ nCcm^{-2}K^{-1}$.

17. A Langmuir-Blodgett film according to claim 16 possessing a static pyroelectric coefficient of from 0.035 to 0.30 $nCcm^{-2}K^{-1}$.

18. A pyroelectric device comprising a film according to claim 16.

* * * * *